(12) United States Patent
Guirguis (10) Patent No.: US 11,389,227 B2
(45) Date of Patent: Jul. 19, 2022

(54) ELECTROSURGICAL DEVICE WITH MULTIVARIATE CONTROL

(71) Applicant: Medtronic Advanced Energy LLC, Minneapolis, MN (US)

(72) Inventor: Mark Guirguis, Stratham, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 880 days.

(21) Appl. No.: 15/208,864

(22) Filed: Jul. 13, 2016

(65) Prior Publication Data

US 2017/0049501 A1 Feb. 23, 2017

Related U.S. Application Data

(60) Provisional application No. 62/207,583, filed on Aug. 20, 2015.

(51) Int. Cl.
*A61B 18/14* (2006.01)
*A61B 18/00* (2006.01)

(52) U.S. Cl.
CPC ...... *A61B 18/1402* (2013.01); *A61B 2018/00029* (2013.01); *A61B 2018/0063* (2013.01); *A61B 2018/00607* (2013.01); *A61B 2018/00702* (2013.01); *A61B 2018/00726* (2013.01); *A61B 2018/00744* (2013.01); *A61B 2018/00922* (2013.01)

(58) Field of Classification Search
CPC ......... A61B 2562/00; A61B 2562/227; A61B 2090/064; A61B 2090/065; A61B 18/1402; A61B 2018/00029; A61B 2018/00922; A61B 2018/00958; A61B 2018/0094; A61B 2560/0487; G06F 3/045
USPC .......................................................... 606/42
See application file for complete search history.

(56) References Cited

U.S. PATENT DOCUMENTS

| | | |
|---|---|---|
| 2,888,928 A | 6/1959 | Seiger |
| 3,682,130 A | 8/1972 | Jeffers |
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |

(Continued)

FOREIGN PATENT DOCUMENTS

| | | |
|---|---|---|
| WO | 96/04955 A2 | 2/1996 |
| WO | 2007/037785 | 4/2007 |
| WO | 2010/141417 | 12/2010 |

OTHER PUBLICATIONS

Interlink Electronics FSR® Force Sensing Resistors. (n.d.), "Force Sensing Linear Potentiometer (FSLP) Integration Guide", Retrieved from https://www.interlinkelectronics.com; 15 pages.

*Primary Examiner* — Thomas A Giuliani
*Assistant Examiner* — Christine A Dedoulis
(74) *Attorney, Agent, or Firm* — Dicke, Billig & Czaja, PLLC (57) ABSTRACT

An electrosurgical device includes a handpiece, an electrode tip extending from the handpiece, the electrode tip configured to deliver an RF signal, and a multivariate controller disposed on the handpiece. The multivariate controller is configured to activate the electrode tip and adjust a setting of the RF signal within a range of settings.

24 Claims, 5 Drawing Sheets

(56) References Cited

U.S. PATENT DOCUMENTS

| | | |
|---|---|---|
| 4,276,874 A | 7/1981 | Wolvek et al. |
| 4,278,090 A | 7/1981 | van Gerven |
| 4,321,931 A | 3/1982 | Hon |
| 4,342,218 A | 8/1982 | Fox |
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,736,749 A | 4/1988 | Lundback |
| 4,779,611 A | 10/1988 | Grooters et al. |
| 4,802,475 A | 2/1989 | Weshahy |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,983,786 A * | 1/1991 | Stevens ............... A61F 4/00 178/18.01 |
| 4,985,030 A | 1/1991 | Melzer et al. |
| 4,998,933 A | 3/1991 | Eggers et al. |
| 5,190,541 A | 3/1993 | Abele et al. |
| 5,195,959 A | 3/1993 | Smith |
| 5,234,428 A | 8/1993 | Kaufman |
| 5,254,117 A | 10/1993 | Rigby et al. |
| 5,281,215 A | 1/1994 | Midler |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Mlilder. |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,271 A | 3/1996 | Burton et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,700 A | 4/1996 | Leone |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,542,196 A | 8/1996 | Hirsch et al. |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Silwa, Jr. et al. |
| 5,562,702 A | 10/1996 | Huitema et al. |
| 5,562,720 A | 10/1996 | Stern et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,605,539 A | 2/1997 | Buelna et al. |
| 5,607,462 A | 3/1997 | Imran |
| 5,617,854 A | 4/1997 | Munsif |
| 5,630,837 A | 5/1997 | Crowley |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,637,090 A | 9/1997 | McGee et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |

(56) References Cited

U.S. PATENT DOCUMENTS

| | | |
|---|---|---|
| 5,718,701 A | 2/1998 | Shai et al. |
| 5,720,775 A | 2/1998 | Lanard. |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,743,903 A | 4/1998 | Stern et al. |
| 5,755,760 A | 5/1998 | Maguire et al. |
| 5,766,167 A | 6/1998 | Eggers et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,905 A | 8/1998 | Fleischman et al. |
| 5,797,960 A | 8/1998 | Stevens et al. |
| 5,735,290 A | 9/1998 | Nelson et al. |
| 5,800,428 A | 9/1998 | Nelson et al. |
| 5,800,482 A | 9/1998 | Pomeranz et al. |
| 5,810,764 A | 9/1998 | Eggers et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,861,021 A | 1/1999 | Thome et al. |
| 5,871,523 A | 2/1999 | Fleischman et al. |
| 5,871,525 A | 2/1999 | Edwards et al. |
| 5,873,845 A | 2/1999 | Cline et al. |
| 5,873,855 A | 2/1999 | Eggers et al. |
| 5,876,399 A | 3/1999 | Chia et al. |
| 5,879,295 A | 3/1999 | Li et al. |
| 5,879,296 A | 3/1999 | Ockuly et al. |
| 5,879,348 A | 3/1999 | Owens et al. |
| 5,881,732 A | 3/1999 | Sung et al. |
| 5,882,346 A | 3/1999 | Pomeranz et al. |
| 5,885,278 A | 3/1999 | Fleischman |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,913,854 A | 6/1999 | Maguire et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,925,045 A | 7/1999 | Reimels et al. |
| 5,927,284 A | 7/1999 | Borst et al. |
| 5,931,810 A | 8/1999 | Grabek |
| 5,931,848 A | 8/1999 | Saadat |
| 5,935,123 A | 8/1999 | Edwards et al. |
| 5,943,044 A * | 8/1999 | Martinelli ............ G06F 3/0488 345/174 |
| 5,944,715 A | 8/1999 | Goble et al. |
| 5,928,191 A | 9/1999 | Houser et al. |
| 5,954,661 A | 9/1999 | Greenspon et al. |
| 5,975,919 A | 9/1999 | Laufer |
| 5,971,980 A | 10/1999 | Sherman |
| 5,971,983 A | 10/1999 | Lesh |
| 5,980,516 A | 11/1999 | Mulier et al. |
| 5,989,248 A | 11/1999 | Tu et al. |
| 5,993,412 A | 11/1999 | Deily et al. |
| 5,993,447 A | 11/1999 | Blewett et al. |
| 6,004,316 A | 12/1999 | Laufer |
| 6,004,319 A | 12/1999 | Goble et al. |
| 6,007,499 A | 12/1999 | Martin et al. |
| 6,010,500 A | 1/2000 | Sherman et al. |
| 6,012,457 A | 1/2000 | Lesh |
| 6,015,391 A | 1/2000 | Rishton et al. |
| 6,016,811 A | 1/2000 | Knopp et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,048,333 A | 4/2000 | Lennox et al. |
| 6,056,744 A | 5/2000 | Edwards |
| 6,056,745 A | 5/2000 | Panescu et al. |
| 6,056,746 A | 5/2000 | Goble |
| 6,056,747 A | 5/2000 | Saadat et al. |
| 6,063,081 A | 5/2000 | Mulier |
| 6,066,139 A | 5/2000 | Ryan et al. |
| 6,068,653 A | 5/2000 | LaFontaine |
| 6,071,279 A | 6/2000 | Whayne et al. |
| 6,083,237 A | 7/2000 | Huitema et al. |
| 6,086,585 A | 7/2000 | Hovda et al. |
| 6,088,894 A | 7/2000 | Oakley |
| 6,096,037 A | 8/2000 | Mulier |
| 6,113,592 A | 9/2000 | Taylor |
| 6,113,596 A | 9/2000 | Hooven et al. |
| 6,117,101 A | 9/2000 | Diederich et al. |
| 6,120,496 A | 9/2000 | Whayne et al. |
| 6,141,576 A | 10/2000 | Littmann et al. |
| 6,142,993 A | 11/2000 | Whayne et al. |
| 6,142,994 A | 11/2000 | Swanson et al. |
| 6,149,620 A | 11/2000 | Baker et al. |
| 6,152,920 A | 11/2000 | Thompson et al. |
| 6,161,543 A | 12/2000 | Cox et al. |
| 6,165,174 A | 12/2000 | Jacobs et al. |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,216,704 B1 | 4/2001 | Ingle et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,231,591 B1 | 5/2001 | Desai |
| 6,235,020 B1 | 5/2001 | Cheng et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |

(56) References Cited

U.S. PATENT DOCUMENTS

| | | |
|---|---|---|
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | Bloom et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,733,497 B2 * | 5/2004 | Messing ............ A61B 18/1492 600/920 |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | Bloom et al. |
| 6,960,205 B2 | 11/2005 | Jahns |
| 6,962,589 B2 | 11/2005 | Mulier |
| 7,066,586 B2 | 6/2006 | da Silva |
| 7,156,845 B2 | 1/2007 | Mulier et al. |
| 7,166,106 B2 | 1/2007 | Bartel et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | Bloom et al. |
| 7,608,072 B2 | 10/2009 | Swanson |
| 7,645,277 B2 | 1/2010 | Bloom et al. |
| 7,651,494 B2 | 1/2010 | Bloom et al. |
| 7,691,050 B2 | 4/2010 | Gellman |
| 7,736,361 B2 | 6/2010 | Palanker |
| 7,811,282 B2 | 10/2010 | McClurken |
| 7,815,634 B2 | 10/2010 | Bloom et al. |
| 7,879,033 B2 * | 2/2011 | Sartor ............... A61B 18/1402 606/45 |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | Bloom et al. |
| 8,105,323 B2 | 1/2012 | Buysse et al. |
| 8,172,828 B2 | 4/2012 | Chang et al. |
| 8,177,783 B2 | 5/2012 | Davison et al. |
| 8,216,233 B2 | 7/2012 | McClurken |
| 8,323,276 B2 | 12/2012 | Palanker et al. |
| 8,348,946 B2 | 1/2013 | McClurken |
| 8,361,068 B2 | 1/2013 | McClurken |
| 8,388,642 B2 | 3/2013 | Muni et al. |
| 8,414,572 B2 | 4/2013 | Davison et al. |
| 8,475,455 B2 | 7/2013 | McClurken |
| 9,107,688 B2 * | 8/2015 | Kimball ......... A61B 17/320068 |
| 2002/0049483 A1 | 4/2002 | Knowlton |
| 2002/0062131 A1 | 5/2002 | Gallo, Sr. |
| 2002/0082643 A1 | 6/2002 | Kammerer et al. |
| 2003/0014050 A1 | 1/2003 | Sharkey et al. |
| 2003/0032954 A1 | 2/2003 | Carranza et al. |

(56) References Cited

U.S. PATENT DOCUMENTS

| | | |
|---|---|---|
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0092927 A1* | 5/2004 | Podhajsky ......... A61B 18/1402 606/42 |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0171525 A1 | 8/2005 | Rioux |
| 2005/0209564 A1 | 9/2005 | Bonner |
| 2005/0267454 A1 | 12/2005 | Hissong |
| 2005/0273097 A1 | 12/2005 | Ryan |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0111709 A1 | 5/2006 | Goble et al. |
| 2007/0024595 A1* | 2/2007 | Baker ................... G06F 3/045 345/173 |
| 2007/0049920 A1 | 3/2007 | Bloom et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0103494 A1 | 5/2008 | Rioux |
| 2008/0207208 A1 | 8/2008 | Schutz |
| 2008/0262489 A1 | 10/2008 | Steinke |
| 2009/0264879 A1 | 10/2009 | Bloom et al. |
| 2009/0306655 A1 | 12/2009 | Stangenes |
| 2010/0069904 A1 | 3/2010 | Cunningham |
| 2010/0100095 A1 | 4/2010 | Bloom et al. |
| 2010/0160906 A1 | 6/2010 | Jarrard |
| 2010/0168743 A1 | 7/2010 | Stone et al. |
| 2010/0204560 A1 | 8/2010 | Salahieh et al. |
| 2010/0241178 A1 | 9/2010 | Tilson et al. |
| 2011/0028965 A1 | 2/2011 | McClurken |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0095461 A1 | 4/2012 | Herscher et al. |
| 2012/0101496 A1 | 4/2012 | McClurken et al. |
| 2012/0116397 A1 | 5/2012 | Rencher et al. |
| 2012/0143293 A1 | 6/2012 | Mauch et al. |
| 2012/0151165 A1 | 6/2012 | Conley et al. |
| 2012/0157989 A1 | 6/2012 | Stone et al. |
| 2012/0184983 A1 | 7/2012 | Chang et al. |
| 2012/0191084 A1 | 7/2012 | Davison et al. |
| 2012/0253343 A1 | 10/2012 | McClurken et al. |

* cited by examiner

ND MULTIVARIATE CONTROL

ELECTROSURGICAL DEVICE WITH MULTIVARIATE CONTROL

CROSS-REFERENCE

This Non-Provisional Utility Application claims benefit to U.S. Provisional Application No. 62/207,583, filed Aug. 20, 2015, entitled "ELECTROSURGICAL DEVICE WITH MULTIVARIATE CONTROL" incorporated herein by reference.

BACKGROUND

This disclosure relates generally to the field of medical devices, systems and methods for use in surgical procedures. More specifically, this disclosure relates to electrosurgical devices, systems and methods that provide for cutting, coagulation, hemostasis, or sealing of bodily tissues including bone with an electrosurgical device.

Electrosurgery includes such techniques as cutting, coagulation, hemostasis, and/or sealing of tissues with the aid of electrodes energized with a suitable power source such as an electrosurgical unit including a power generator. Typical electrosurgical devices apply an electrical potential difference or a voltage difference between an active electrode and a return electrode on a patient's grounded body in a monopolar arrangement or between an active electrode and a return electrode on the device in bipolar arrangement to deliver electrical energy to the area where tissue is to be affected. The electrosurgical device are typically held by the surgeon and connected to the power source, such as the electrosurgical unit, via cabling.

In one example, an electrical signal, such as voltage, is applied either as a train of high frequency pulses or as a continuous signal typically in the radiofrequency (RF) range. The signals could include a set of parameters, such as power or voltage level parameters, waveform parameters such as frequency, pulse duration, duty cycle, and other signal parameters. For example, a surgeon could use a monopolar electrosurgical device to cut tissue and control bleeding. Tissue could be cut using a first RF signal having a set of parameters and bleeding could be controlled using a second RF signal having another set of parameters. The surgeon could also use a bipolar electrosurgical device for hemostatic sealing of the tissue that would employ a third RF signal having a unique set of parameters.

Surgical parameters, including the parameters related to RF energy as well as fluid flow and other parameters are typically set and adjusted on the electrosurgical unit. The electrosurgical device, which is includes the active electrode, are handheld and include activation switches, such as pushbuttons, to delivery the RF energy to the active electrode during surgery.

When different functions were performed during a surgical procedure, surgeons would switch between different devices or adjust settings located on the electrosurgical units. Switching between devices and adjusting settings for the devices can lead to undesirable effects such as longer procedure times, longer response times to issues that unexpectedly develop during surgery, higher costs, and an increased likelihood of inaccuracy or imprecision.

To address these issues, some electrosurgical devices capable of performing multiple functions, such as cutting and coagulating in a monopolar mode, or operating in multiple modes, such as both monopolar and bipolar modes, have been developed. Several such electrosurgical device are described, for example, in U.S. Pat. No. 8,632,533 to Greeley, et al., U.S. Patent Application Publication No. 2012/0004657 to Conley, et al., U.S. Patent Application Publication No. 2011/0178515 to Bloom et al., each assigned to the assignee of the present disclosure and incorporated by reference herein in their entireties to the extent they are not inconsistent with the present disclosure.

Multifunction electrosurgical devices or electrosurgical devices having multiple features, however, can create concerns for surgeons. For example, such devices generally have dedicated inputs in the form of wires and cords corresponding for each function or feature that adds size and weight to the electrosurgical device and decreases flexibility of the input cable, which can result in hand strain for the surgeon. Additionally, each of these functions or features may require an activation mechanism, such as a pushbutton on the handpiece or other activation mechanism that may cause confusion for the surgeon increase the size of the device. Adding functions and features to electrosurgical devices increase these concerns and diminish from the utility of the device.

SUMMARY

This summary is provided to introduce a selection of concepts in a simplified form that are further described below in the Detailed Description.

The disclosure relates to an electrosurgical device having a handpiece that includes a multivariate controller including a transmission element to enable activation and the adjustments of one or more surgical parameters from the handpiece during surgery. In one example, the multivariate controller can be used to actuate the electrosurgical device and adjust settings of RF power, RF waveform, fluid flow, or other features or parameters used during surgery from the handpiece rather than from a remote electrosurgical unit electrically coupled to the handpiece. In one example, the multivariate controller can be used to adjust settings and or change functions between hemostatic sealing, cutting, and coagulation. A user such as a surgeon can touch or apply a force to the multivariate controller, and one or more settings or surgical parameters can be adjusted with a single touch.

In one example, the multivariate control includes a transmission element. The transmission element can be used in place of actuating pushbuttons or in addition to binary actuating switches. The transmission element includes a section referred to as an active portion that can sense a position of touch as well as a force of the touch on the active portion. In one example, three conductors from the transmission element are provided to the electrosurgical unit through the handpiece cabling. One conductor can be used to energize the element with a voltage while the other two conductors can be used to decipher position and force of the touch. The transmission element is modeled as a resistor network that alters as force is applied and also changes depending where that force is applied on the active area. The location and force of the touch is used to control multiple surgical parameters, such as power level and waveform of the RF energy provided to the electrode. One implementation of this may be to positively correlate increasing force with increasing power. Additionally, force applied on one end of the element may correlate with a cut waveform, and the other end with a coagulation waveform.

In one aspect, the disclosure is directed to an electrosurgical device including a handpiece, an electrode tip extending from the handpiece, the electrode tip configured to deliver an RF signal, and a multivariate controller disposed on the handpiece. The multivariate controller is configured to activate the electrode tip and adjust a setting of the RF signal within a range of settings.

In another aspect, the disclosure is directed to an electrosurgical device including a handpiece, an electrode tip extending from the handpiece, the electrode tip configured to deliver an RF signal, and a multivariate controller. The multivariate controller includes a mounting piece disposed within the handpiece, and a transmission element disposed on the mounting piece. The transmission element is configured to detect an amount of force applied to the multivariate controller and responsively adjust a setting of the RF signal within a range of settings.

In still another aspect, the disclosure is directed to an electrosurgical device including a handpiece, an electrode tip extending from the handpiece, the electrode tip configured to deliver an RF signal, and a force sensing linear potentiometer. The force sensing linear potentiometer includes an active surface disposed on the handpiece configured to activate the electrode tip and adjust a setting of the RF signal within a range of settings with a force applied to the active surface to adjust an impedance.

In still another aspect, the disclosure is directed to an electrosurgical device including a handpiece, an electrode tip extending from the handpiece, wherein the electrode tip configured to deliver an RF signal. The electrosurgical device also includes a multivariate controller coupled to the handpiece and configured to activate the electrode tip and adjust a setting of the RF signal within a range of settings. The multivariate controller includes a first conductive drive line and a second conductive drive line and a conductive sense line coupled to a touch spot on the potentiometer.

DETAILED DESCRIPTION

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

Figure 1:
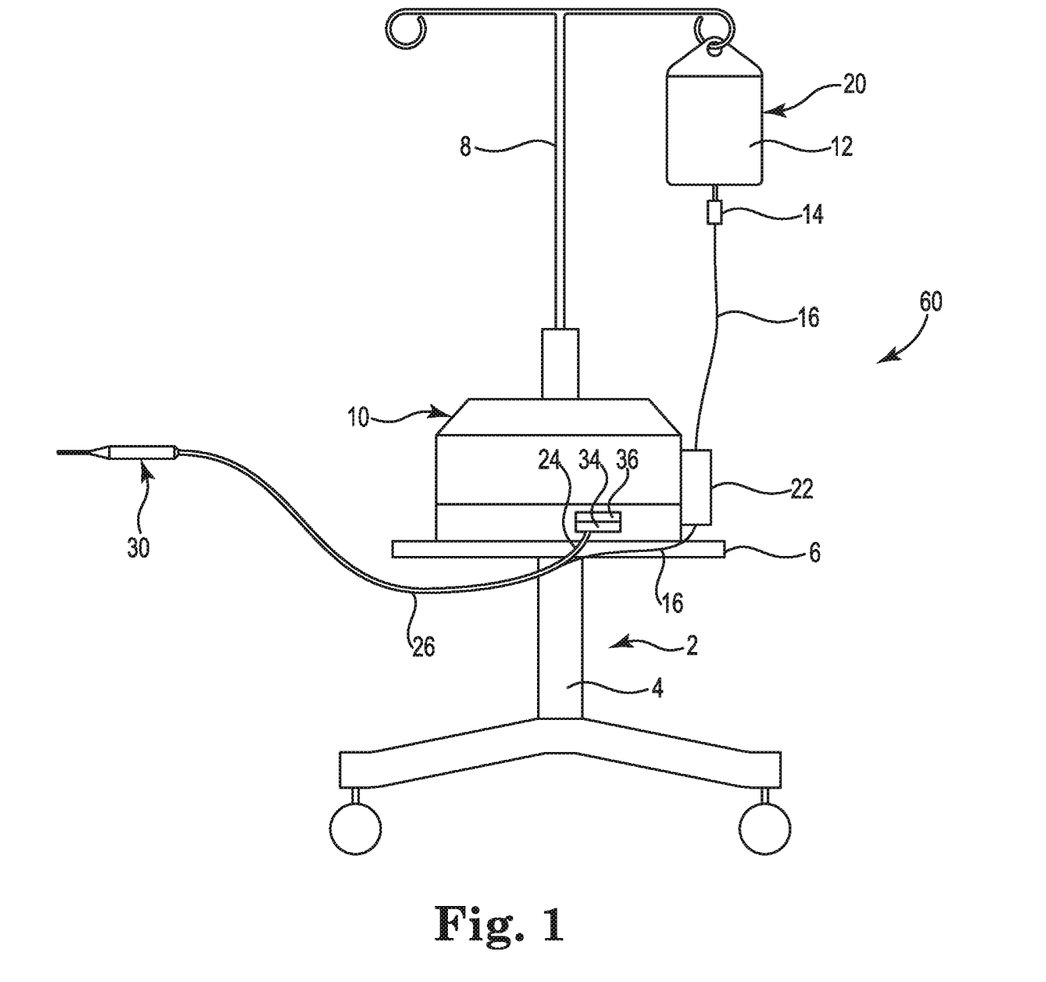
FIG. 1 is a front view of an embodiment of a system according to the present disclosure including an example electrosurgical unit in combination with a fluid source and handheld electrosurgical device.

FIG. 1 illustrates a front view of one example of a system 60 that includes an electrosurgical unit 10 in combination with an example handheld electrosurgical device 30. The device 30, in one example, can be configurable for use in cutting and sealing, including electrocautery, coagulation in a monopolar mode. In another example, device 30 can be configured to provide for hemostatic sealing of tissue including bone in a bipolar mode. In still another example, device 30 can be configurable in both monopolar and bipolar modes. In some examples, device 30 can be used in combination with a fluid source 20, such as for hemostatic sealing or for other electrical surgical procedures.

The system 60 can be carried on a movable cart 2 having a support member 4 comprising a hollow cylindrical post which includes a platform 6 comprising a pedestal table to provide a flat, stable surface for location of the electrosurgical unit 10. Cart 2 can include a pole 8 having a height that can be adjusted by sliding the pole 8 up and down. Fluid source 20 can be supported at the top of pole 8.

Fluid source 20 may comprise a bag of fluid from which fluid 12 may flow through a drip chamber 14, to delivery tubing 16 and to handheld electrosurgical device 30. In one example, the fluid 12 includes saline and can include physiologic saline such as sodium chloride (NaCl) 0.9% weight/volume solution. Saline is an electrically conductive fluid, and other suitable electrically conductive fluids can be used. In other examples, the fluid may include a nonconductive fluid, such as deionized water, which may still provide advantages over using no fluid and may support cooling of portions of electrosurgical device 30 and tissue or reducing the occurrence of tissue sticking to the electrosurgical device 30.

The fluid delivery tubing 16 in the example passes through pump 22 to convey fluid to the electrosurgical device 30 and control fluid flow. Pump 22 in one example is a peristaltic pump such as a rotary peristaltic pump or a linear peristaltic pump. A peristaltic pump can convey the fluid through the delivery tubing 16 by way of intermittent forces placed on the external surface of the delivery tubing. Peristaltic pumps are often applied during use of the electrosurgical device 30 because the mechanical elements of the pump places forces on the external surface of the delivery tubing and do not come into direct contact with the fluid, which can reduce the likelihood of fluid contamination. Other examples of system 60 might not include a pump, and fluid can be is provided to the electrosurgical device 30 via gravity.

The example electrosurgical unit 10 can provide monopolar, bipolar, or both monopolar and bipolar radio-frequency (RF) power output to a specified electrosurgical instrument such as electrosurgical device 30. In one example, the electrosurgical unit 10 can be used for delivery of RF energy to instruments indicated for cutting and coagulation of soft tissue and for delivery of RF energy concurrent with fluid to instruments indicated for hemostatic sealing and coagulation of soft tissue and bone. In one example, the electrosurgical unit 10 is capable of simultaneously powering specified monopolar and bipolar electrosurgical instruments but may include a lock out feature preventing both monopolar and bipolar output from being simultaneously activated.

During monopolar operation of electrosurgical device 30, a first electrode, often referred to as the active electrode, is provided with electrosurgical device 30 while a second electrode (not shown), often referred to as the indifferent or neutral electrode, is provided in the form of a ground pad dispersive electrode located on a patient. For example, the ground pad dispersive electrode is typically on the back, buttocks, upper leg, or other suitable anatomical location during surgery. In such a configuration, the ground pad dispersive electrode is often referred to as a patient return electrode. An electrical circuit of RF energy is formed between the active electrode and the ground pad dispersive electrode through the patient.

In some examples, the handheld electrosurgical device may have two or more active electrodes for use in monopolar mode. One such device is described in U.S. Pat. No. 8,414,572 to Davidson et al., and assigned to the assignee of the present disclosure and incorporated by reference herein in its entirety to the extent it is not inconsistent with the present disclosure. One of the electrodes can be activated to perform first function, such as a cut function, and another can be activated to perform a second function, such as a coagulation function or other function and used in combination with the ground pad dispersive electrode. The two or more active electrodes can be electrically isolated from one another.

During bipolar operation of electrosurgical device 30, a second electrode, often referred to as the return electrode providing a second electrical pole, is provided as part of the device 30. The ground pad dispersive electrode is not used. An electrical circuit of RF energy is created between the first and second poles of the device 30. The current no longer flows through the patient's body to the ground pad dispersive electrode, but rather through a localized portion of tissue between the poles of the device 30.

The electrosurgical device 30 in the example is connected to electrosurgical unit 10 via cable 24. Cable 24 includes plugs 34 that connect with receptacles 36 on the electrosurgical unit 10. In one example, a receptacle can correspond with an active electrode receptacle and one or more receptacles can correspond with controls on the electrosurgical device 30. Still further, a receptacle can correspond with a return electrode receptacle for devices that can be operated in a bipolar mode. If the electrosurgical unit 10 may be used in monopolar mode, an additional cable may connect a ground pad electrode to a ground pad receptacle of the electrosurgical unit 10. In some examples, delivery tubing 16 and cable 24 are combined to form a single cable 26.

The features of electrosurgical unit 10 described are for illustration, and the electrosurgical units suitable for use with device 30 may include some, all, or other features than those described below. In one example, the electrosurgical unit is capable of operating in monopolar and bipolar modes as well as multiple functions within a mode such as a monopolar cutting function and a monopolar coagulation function. In some examples, a monopolar device is capable of performing a monopolar hemostasis or tissue sealing function. In the monopolar cutting function, monopolar RF energy is provided to the device 30 at a first power level and/or a first waveform (collectively first RF energy setting). For example, RF energy for a cut function may be provided at a relatively low voltage and a continuous current (100% on, or 100% duty cycle). Nominal impedance can range between 300 to 1000 ohms for the cutting function. At a power setting of 90 Watts for cutting, voltage can range from approximately 164 to 300 volts root mean square (RMS). In the monopolar coagulation function, monopolar RF is energy is provided to the electrode at a second power level and/or second waveform (collectively second or coagulation RF energy setting) that is different than at least one of the first power level or the first waveform. For example, RF energy for a coagulation function may be provided at a relatively higher voltage than the cut voltage and with a pulsed current, such as 1% to 6% on and 99% to 94% off, respectively (or 1% to 6% duty cycle). Other duty cycles are contemplated. The electrosurgical unit 10 in the bipolar mode may provide bipolar RF energy at a third power level and/or third waveform (collectively third RF energy setting) to the device 30 along with a fluid for a (generally low voltage) hemostasis or tissue sealing function that may the same as or different than the cutting and coagulation RF settings provided to the device 30 for the cut function or the coagulation function. In one example, hemostatic sealing energy can be provided with a continuous current (100% duty cycle). Nominal impedance can range between 100 to 400 ohms for the hemostatic sealing function. At a power setting of 90 Watts for hemostatic sealing, voltage can range from approximately 95 to 200 volts RMS.

In one example, the unit 10 provides RF energy to the active electrode as a signal having a frequency in the range of 100 KHz to 10 MHz. Typically this energy is applied in the form of bursts of pulses. Each burst typically has a duration in the range of 10 microseconds to 1 millisecond. The individual pulses in each burst typically each have a duration of 0.1 to 10 microseconds with an interval between pulses of 0.1 to 10 microseconds. The actual pulses are often sinusoidal or square waves and bi-phasic, that is alternating positive and negative amplitudes. Several other features are described in U.S. Pat. No. 8,323,276, to Palanker et al., and incorporated by reference herein in its entirety to the extent it is not inconsistent with the present disclosure.

The electrical surgical unit 10 includes a power switch to turn the unit on and off and an RF power setting display to display the RF power supplied to the electrosurgical device 30. The power setting display can display the RF power setting numerically in a selected unit such as watts.

The example electrosurgical unit 10 includes an RF power selector comprising RF power setting switches that are used to select or adjust the RF power setting. A user can push one power setting switch to increase the RF power setting and push the other power setting switch to decrease the RF power setting. In one example, power setting switches are membrane switches, soft keys, or as part of a touchscreen. In another example, the electrosurgical unit may include more than one power selectors such as a power selector for monopolar power selection and a power selector for bipolar power selection.

In one example, the electrosurgical unit 10 provides the power to the device 30, but the actual power level delivered to the electrosurgical device 30 is selected via controls on the electrosurgical device 30 rather than controls on the electrosurgical unit 10. In another example, the electrosurgical unit 10 can be programmed to provide power levels within a selected range of power, and the electrosurgical device 30 is used to select an output power level within the preprogrammed range.

For instance, the unit 10 can be programmed to provide monopolar energy for a cut function in a first range of power settings. The unit 10 can be programmed to provide monopolar energy for a coagulation function in a second range of power settings, which second range may be the same as, different than, or overlap the first range. The surgeon may then select the function and adjust the power setting within the range using controls on the device 30 rather than using controls on the unit 10. Other examples of controlling power setting with controls on the device 30 rather than with controls on the unit 10 are contemplated.

The example electrosurgical unit 10 can also include fluid flow rate setting display and flow rate setting selector. The display can include indicator lights, and the flow rate selector can include switches. Pushing one of the flow rate switches selects a fluid flow rate, which is than indicated in display.

While not being bound to a particular theory, the relationship between the variables of fluid flow rate Q (such as in units of cubic centimeters per minute (cc/min)) and RF power setting $P_S$ (such as in units of watts) can be configured to inhibit undesired effects such as tissue desiccation, electrode sticking, smoke production, char formation, and other effects while not providing a fluid flow rate Q at a corresponding RF power setting $P_s$ not so great as to disperse too much electricity and or overly cool the tissue at the electrode/tissue interface. Electrosurgical unit 10 is configured to increase the fluid flow rate Q generally linearly with an increasing RF power setting $P_S$ for each of the three fluid flow rate settings of low, medium, and high.

Electrosurgical unit 10 can be configured to include control of the pump 22. In this example, the speed of the pump 22, and the fluid throughput, can be predetermined based on input variables such as the RF power setting and the fluid flow rate setting. In one example, the pump 22 can be integrated with the electrosurgical unit 10.

In one example, the electrosurgical unit via pump provides the fluid 12 to the device 30, but the actual rate of fluid flow delivered to the electrosurgical device 30 is selected via controls on the electrosurgical device 30 rather than controls on the electrosurgical unit 10. In another example, the electrosurgical unit 10 can be programmed to provide fluid flow rate within a selected range of rates of flow, and the electrosurgical device 30 is used to select fluid flow rate within the programmed range.

For instance, the unit 10 can be programmed to provide fluid flow rate for monopolar operation in a first range of fluid flow settings. The unit 10 can be programmed to provide fluid flow for bipolar operation in a second range of fluid flow rate settings, which second range may be the same as, different than, or overlap the first range. The surgeon may then select the mode and adjust the fluid flow rate within the range using controls on the device 30 rather than using controls on the unit 10. Other examples of controlling fluid flow with controls on the device 30 rather than with controls on the unit 10 are contemplated.

While electrosurgical surgical device 30 is described with reference to electrosurgical unit 10 and other elements of system 60, it should understood the description of the combination is for the purposes of illustrating system 60. It may be possible to use the electrosurgical device 30 in other systems or the electrosurgical unit 10 may be used with other electrosurgical devices.

Power setting and fluid flow are two examples of variables that may be controlled and adjusted, in whole or in part, at the electrosurgical device 30 rather than at the electrosurgical unit 10. Other examples are contemplated. Further, the electrosurgical device may include multiple configurations, such as multiple functions of cutting, coagulating, hemostatic sealing or multiple modes such as bipolar and monopolar. Other examples are contemplated. Each one of these configurations may include adjustable variables in addition to binary activation, such as on/off. Examples of electrosurgical devices with an adjustable variable control or multivariate controls are described below.

Moving control features from the electrosurgical unit to the handheld electrosurgical device, however, is replete with difficulties. For example, added wiring and components to the handheld electrosurgical device and cable to the device increases the weight and reduces the flexibility of the device, which results in fatigue and hand strain, and creates a less ergonomically sound device. Further, the added functions can create confusion for the user. Still further, some components used to perform or detect adjustments are not suited for use at the surgical site either because they are sensitive to the surgical environment or the noise and fields generated with high-powered RF signals.

Figure 2:
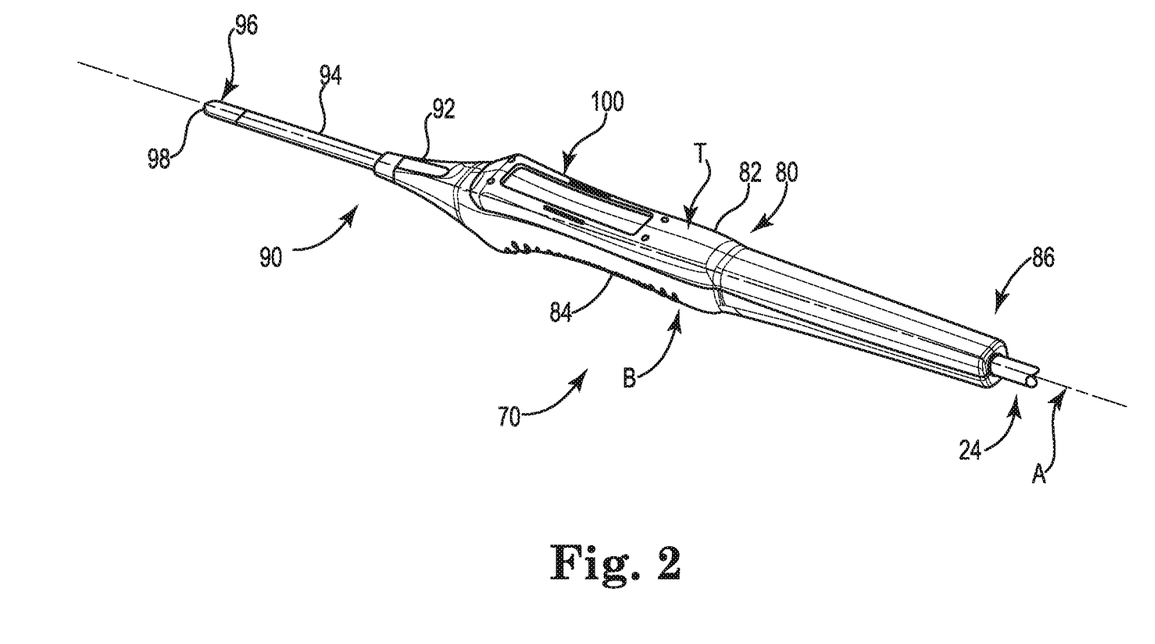
FIG. 2 is a perspective view of an example of the handheld electrosurgical device of FIG. 1 including a multivariate control.

FIG. 2 illustrates one example of a monopolar electrosurgical device 70, which can provide an example of electrosurgical device 30, having an adjustable variable or multivariate control. In the example, the electrosurgical device 70 is operable in a first function, such as a cut function, with a variable power setting and operable in a second function, such as a coagulation function with a variable power setting. Controls for selecting the function and the respective power setting are located on the device 70, such as on multivariate controller 100.

Electrosurgical device 70 extending along longitudinal axis A includes a handpiece 80. Handpiece 80 includes a handle 82 having a finger grip portion 84 with ridges shown on the lower surface or bottom B of the device 70 and intended to be held in the surgeon's hand. The handpiece 80 includes a proximal end 86 for balance and, in the example, includes an electrical connector for electrically coupling cable 24 to the device 70. The electrosurgical device 70 can include an electrode assembly 90 extending distally from the handpiece 80. The electrode assembly 90 in the example includes a body portion 92 attached to a shaft 94. The shaft 94 carries one or more electrical leads to an electrode tip assembly 96 on a distal end of the shaft 94. The electrode tip assembly 96 includes a distal tip 98 that is, in the example, shaped like a blade.

Electrodes and electrically conductive paths and contacts in electrosurgical device 70 can be formed from electrically conductive material such as metal and may comprise stainless steel, titanium, gold, silver, platinum or any other suitable material. Electrical pathways within the device 70 can be formed as wires, traces, or other pathways.

In the example, the shaft 94 includes a fluid lumen for fluidly coupling to delivery tubing 16 and having an outlet port disposed on the electrode tip assembly 96 for selectively dispersing fluid 12.

Handpiece 80 may be configured to enable a user of electrosurgical device 70 to hold and manipulate device 70 between the thumb and index finger like a writing instrument or an electrosurgical pen. Handpiece 80 may comprise a sterilizable, rigid, electrically insulative material, such as a synthetic polymer (e.g., polycarbonate, acrylonitrile-butadiene-styrene). The handle 82 can include an upper surface, or top T, opposite bottom B. Multivariate controller 100 in the example is disposed on top T and configured to be operated by the user's thumb or index finger. Alternate configurations are contemplated.

Multivariate controller 100 in the example provides power, waveform, and activation control or adjustment on the handpiece 80. Typically, electrosurgical units include settings such as power and waveform control and adjustment on the unit interface, and a handpiece only includes a binary activation (on/off) control. Some of the advantages of device 70 are that the user, such as a surgeon, will save time by being able to make adjustments to variables such as power and waveform as opposed to having to stop and either make the adjustments on the electrosurgical unit or request someone else to adjust the settings on the electrosurgical unit. It will also enable the user to more quickly react to unforeseen events, such as inadvertently cutting a blood vessel, by being able to quickly switch between cutting and coagulation modes as well as increasing power during activation.

Accordingly, the multivariate controller 100 is able to activate the electrode assembly 90 as well as adjust a setting of an RF signal to the electrode assembly 90 or electrode tip assembly 96. The multivariate controller 100 is distinguishable from a binary actuation control, such as an on/off switch, in that a multivariate controller 100 can adjust one or more settings of the signals to the electrode assembly 90 or functions of the handpiece 80.

In one example, the handpiece 80 includes a multivariate controller 100 to adjust settings of the RF signal as well as to activate the electrode assembly 90. In another example, the handpiece 80 includes a multivariate controller to adjust setting of the RF signal and a binary actuation control to activate the electrode assembly 90. The multivariate controller 100 can include conductors operably coupled to electrosurgical unit 10 to adjust the settings or adjust the settings of within a preprogrammed or user-selected range of values. The binary actuation controller can include a switch to selectively provide the RF signal from the electrosurgical unit 10 to the electrode tip 90.

Figure 3:
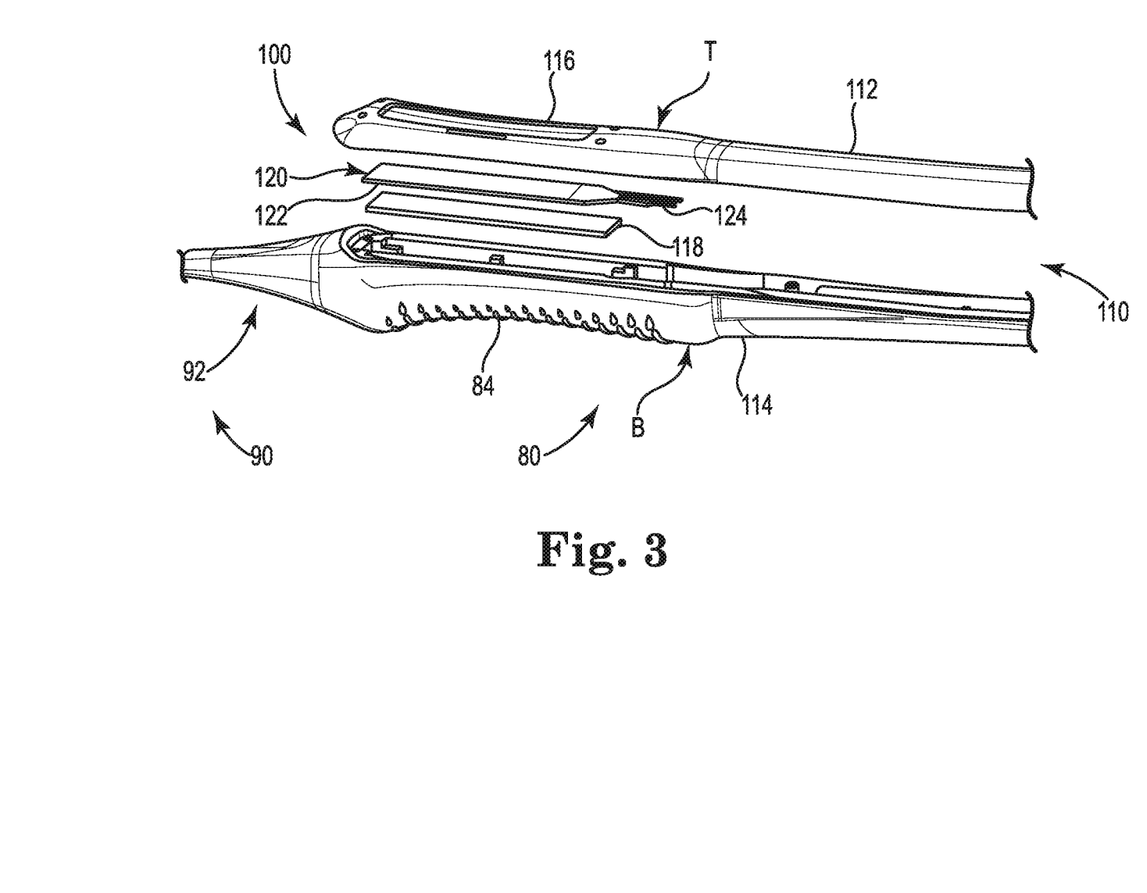
FIG. 3 is an exploded view of the example handheld electrosurgical device of FIG. 2 showing features of an example multivariate controller.

FIG. 3 is a partially exploded view of the example device 70 of FIG. 2 illustrating features of the multivariate controller 100. In the example, the handpiece 80 includes a multi-piece cover 110 including a top cover 112 and a bottom cover 114 having the finger grip portion 84. The top cover 112 includes a generally smooth, possibly flat, controller cover 116 defining an active surface that is deflectable under force, such as under the force of user pressing on the deflectable controller cover 116 with a finger or thumb. In one example, the deflectable controller cover 116 can be integrally formed with the top cover 112 but manufactured to include a relatively thin, planar or smooth surface for the deflectable controller cover 116. The multivariate controller 100 further includes a relatively rigid mounting piece 118 under the active surface of the deflectable cover 116. In the example, the mounting piece 118 is relatively rigid as compared to the deflectable controller cover 116 and includes a smooth surface generally free of bumps or ridges. In the example shown, the mounting piece 118 includes a flat surface and can be rigidly supported against the bottom cover 114 with internal structures or potting material (not shown). In another example, the smooth surface of the mounting piece follows the shape of the deflectable cover 116.

In one example, the multivariate controller 100 includes a transmission element 120 that senses force and, in the example, can sense position of a force on the controller cover 116. The transmission element disposed between the controller cover 116 underneath the active surface and above the rigid mounting piece 118. In one example, the transmission element 120 is embedded in the handpiece 80 in place of the actuating pushbuttons coupled to switches. In one example, the transmission element 120 can sense a position of the force on the controller cover 116 along the longitudinal axis A. In another example, the transmission element 120 can sense a position of the force on two dimensions of the controller cover 116 including along longitudinal axis A and a lateral dimension.

The transmission element 120 includes an active portion 122 and a tail portion 124. The active portion 122 is disposed underneath the active surface of the controller cover 116 and is responsive to the active surface being deflected under a force. The active portion 122 can be urged against the underside of the active surface of the controller cover 116 to preload the transmission element so the transmission element 120 will respond under less force applied to the controller cover 116. In one example, the tail portion 124 includes conductors electrically coupled to the active portion 122 that are also electrically routed to the electrosurgical unit 10 through the cable 24. One conductor will energize the active portion 122 with a voltage while other conductors are used to decipher force and, in some examples, position when the multivariate controller 100 is pressed or deflected on the active surface.

In some examples, the multivariate controller 100 can include more than one transmission element that is capable of sensing force or more than one transmission element that is capable of sensing force and position, such as linear position, to provide for multivariate control and adjustment in addition to binary activation. Additionally, the multivariate controller 100 may include more than one controller cover 116 and/or more than one mounting piece 118. The controller cover 116 is provided to protect the transmission element 120. In some applications, the transmission element 120 will be durable enough to interface directly with the user, and the controller cover may be absent.

The transmission element is modeled as a circuit element network that alters as force is applied and also changes depending where that force is applied on the active surface. The electrosurgical unit 10 can use information on position of deflection and force of deflection to control power and waveform, such as by adjusting the power and duty cycles, for example, within certain ranges. One implementation may be to positively correlate increasing force with increasing power. Additionally, force applied on one sub-area of the active surface, corresponding with one sub-area of the active portion 122 (such as one end of the multivariate controller) may correlate to a pure cut waveform, and another sub-area (such as the other end of the multivariate controller 110) with a coagulation waveform.

Figure 4:
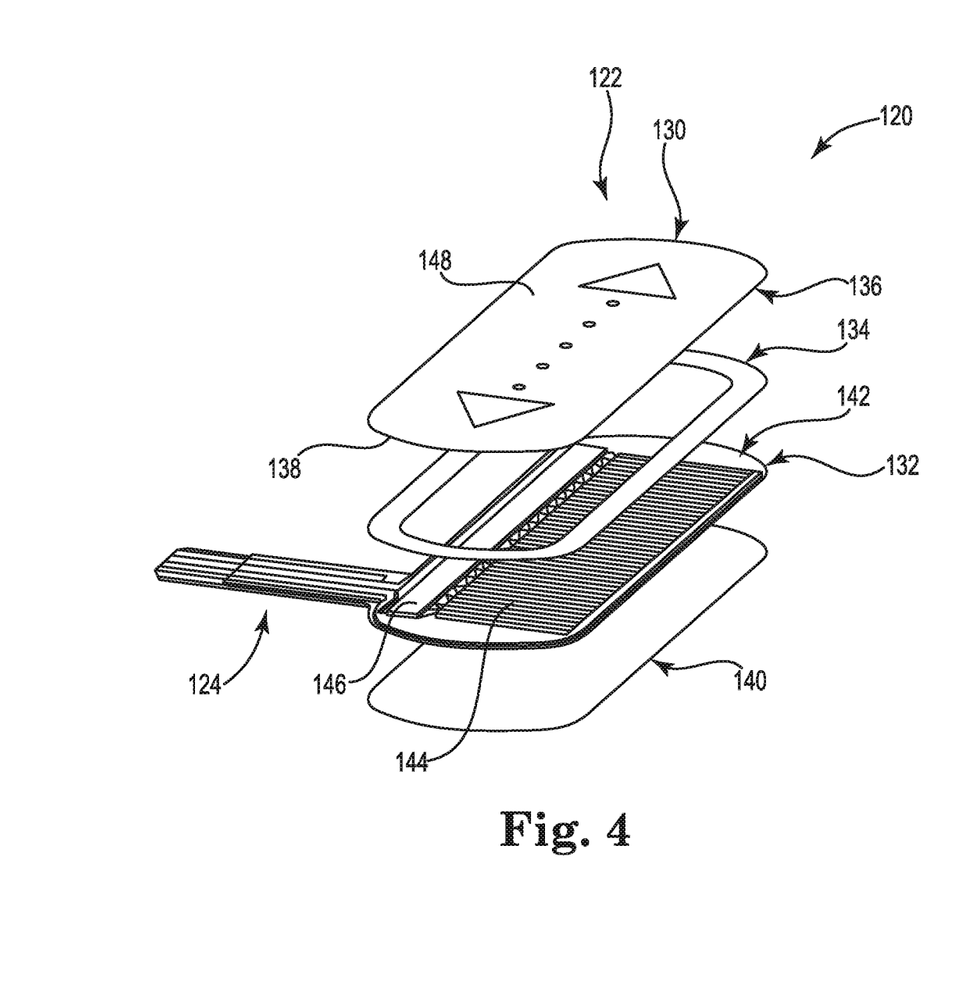
FIG. 4 is an exploded view illustrating an example transmission element of the multivariate controller of FIG. 3.

FIG. 4 is an exploded view of features of an example transmission element 120. Transmission element 120 of the example includes membranes separated by an air gap, or more particularly, a conductive membrane 130 and a conductor substrate 132. An adhesive spacer 134 disposed around the edges of the active portion 122 maintains the air gap between the two relatively rigid membranes 130, 132. The transmission element 120 can also include an adhesive layer 140 affixed to the underside of conductor substrate 132 to attach the transmission element to the device 70, such as at the mounting piece 118. The adhesive in the adhesive layer 140 and spacer 134 can be a pressure sensitive adhesive.

The conductive membrane 130 in the example includes an under surface 136 coated with a conductive ink 138, such as a carbon-based ink. The conductive member 130 also includes an upper surface 148 that may include indicia for directing a user to operate the device, such as arrows or markings. In general, the upper surface 148 is non conductive and is configured to be durable to the touch. In one example, a user can directly touch the upper surface 148.

The conductor substrate 132 in the example includes an upper surface 142 having set of interdigitated traces 144 electrically isolated from each other. When the membranes 130, 132 are pressed together, the ink 138 short circuits the interdigitated traces 144, or electrically couples the interdigitated traces together, with a resistance that is related to the force applied.

In the case of a force-sensing resistor, the conductor substrate can include two electrically-isolated sets of interdigitated traces, each having a conductor on the tail portion. In this respect, the transmission element acts as a potentiometer where force affects the impedance, or resistance, that can be detected by the electrosurgical unit 10. Increasing the force on the active area decreases the resistance of the transmission element.

The electrosurgical unit 10 can be configured to detect the amount of force applied on the active area by measuring, either directly or inferentially, the resistance of the transmission element, and thus provide an corresponding adjusted parameter to the electrosurgical device. For example, a user can increase the force on the active area to increase power of the RF signal provided to the electrode. Alternatively, the a user can increase the force on the active area to increase the duty cycle of a waveform, increase the fluid dispersed at the electrode, or other adjustment in parameter. An element configured to detect only force can provide, for example, one adjusted parameter as well as activation of the electrode.

In the example shown, the transmission element 120 is configured as a force sensing linear potentiometer that can both detect force and linear position of a touch or press on the active portion 122. Signals from the active portion 122 are provided to a sense line and a pair of drive lines in the tail 124. The interdigitated traces 144 are configured as conductive fingers, such as fingers formed from silver, that orthogonally protrude along the length of the active portion 122. In addition to the traces 144, the upper surface 142 of the conductive substrate 132 also includes a fixed resistor 146. The conductive fingers are interdigitated with a sense line in the tail 124. When the membranes 130, 132 are pressed together, the sense line is shorted to a point along the fixed resistor 146 through the orthogonally protruding fingers of the traces 144. The resistance from either drive line to the touch point is proportional to the location of the touch along the length of the fixed resistor 146.

Other force sensing transmission elements are contemplated. For example, the transmission element may include multidimensional position sensing (position sensing on a two-dimension surface) that can include additional force sensing for control of additional variables in addition to or instead of linear position and force sensing. Resistive circuits as described above can be used in a variety of environments, are particularly adapted to detecting force, and are not dependent on local electrical fields so it can be activated using gloves, but other sensing circuits, such as capacitive circuits, can be employed for multivariate controls.

Figure 5:
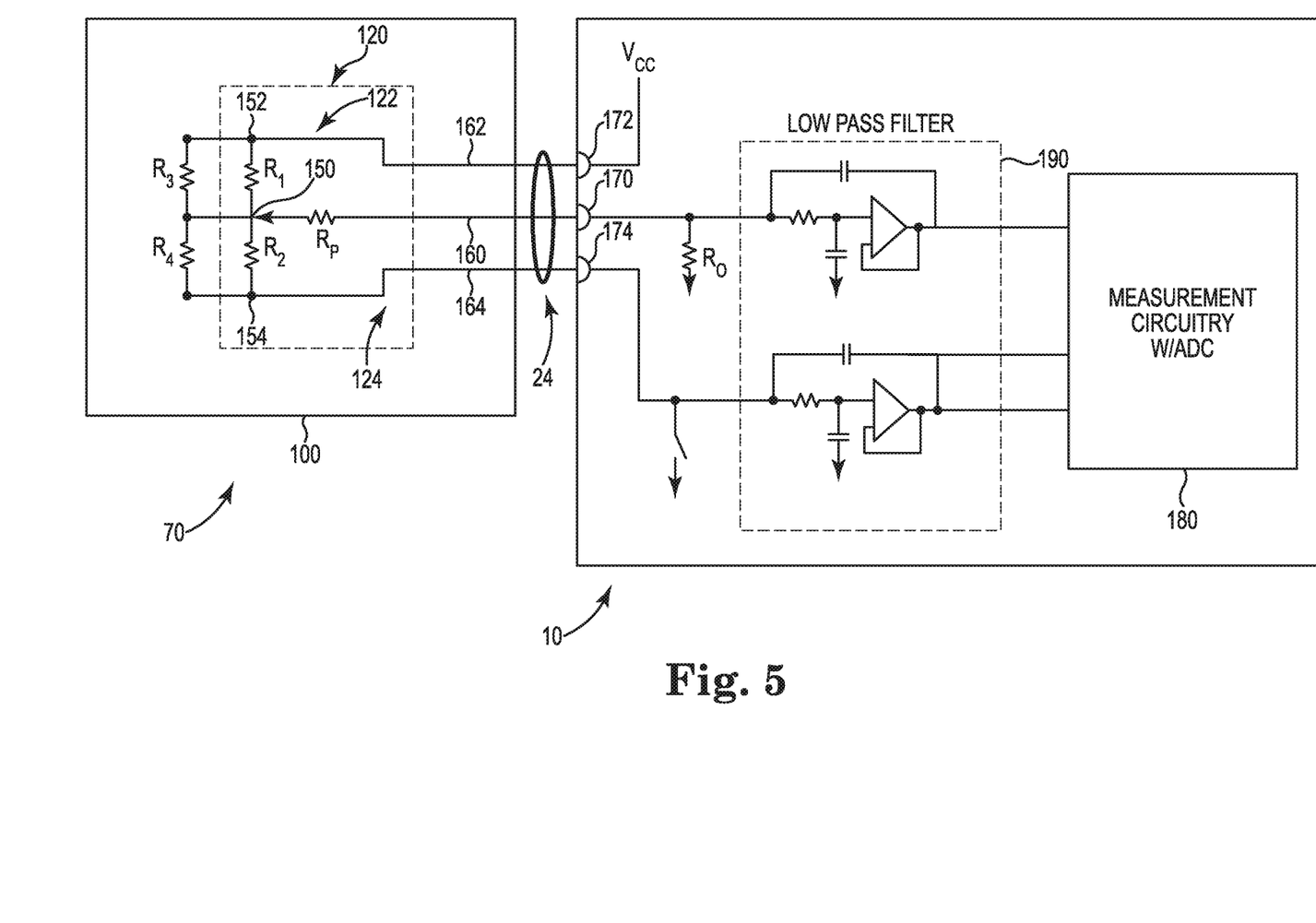
FIG. 5 is a schematic circuit diagram of the electrosurgical device of FIG. 3 in combination with an electrosurgical unit, such as an electrosurgical unit of FIG. 1.

FIG. 5 is a schematic circuit diagram illustrating relevant portions of the electrosurgical device 70 including the multivariate controller 100 having transmission element 120 in combination with an example electrosurgical unit 10. The multivariate controller 100 includes transmission element 120 having a first sensor terminal 152 coupled to a first drive line 162 and a second sensor terminal 154 coupled to a second drive line 164. The multivariate controller 100 also includes a sense line 160 that is coupled in series with a touch spot 150 on the active portion. Drive lines 162, 164, and sense line 160 are electrically coupled from the tail portion 124 to the cabling 24 to extend to the electrosurgical unit 10 in one example.

The transmission element 120 is a three-terminal device and when touched, has a circuit that can be modeled as three resistors. $R_1$ is the resistance on drive line from sensor terminal 152 to the touch spot 150. $R_2$ is the resistance on drive line from the touch spot 150 to sensor terminal 154. Rp is connected to the junction between $R_1$ and $R_2$ by the user's touch. As the user varies the touch spot from one end of the transmission element 120 to the other end of the transmission element, $R_1$ becomes larger and $R_2$ becomes smaller. As the user presses harder, Rp decreases. Rp varies from around 300 kilo-ohms (k$\Omega$) at light touches to 2k$\Omega$ at heavy touches. The resistance is related, and roughly proportional, to the reciprocal of the force.

In some example, the resistance of the transmission element may be too large to be accurately detected with the circuitry of the electrosurgical unit 10. In such examples, the resistance can be reduced by placing additional resistors in parallel with the resistors on the drive lines 162, 164. For example, the multivariate controller 100 can include resistors $R_3$, $R_4$, as shown, disposed between the first sensor terminal 152 and touch spot 150 and touch spot 150 and second sensor terminal 154, respectively. In one example, resistors $R_3$, $R_4$ are disposed in the handpiece 80. In other examples, the resistors $R_3$, $R_4$ can be disposed in the electrosurgical unit 10. In still other examples, the resistors can be absent and the sense circuitry in the electrosurgical unit can be configured to work with the transmission element 120 with or without additional circuit elements to reduce resistance.

In the example, the electrosurgical unit 10 includes input/output receptacles 170, 172, 174 configured to correspond with and receive lines 160, 162, 164, respectively, and to detect force and position of touch spot on transmission element 120 with measurement circuit 180. In one example, measurement circuit 180 includes analog to digital converters electrically coupled to receptacles 170, 174 to detect and convert a voltage or other signal from lines 160, 164 and convert to a corresponding measurement value, such as an eight bit digital input having 256 settings. In the example, receptacle 172 is electrically coupled to an input voltage, such as a power supply voltage. In one example, the electrosurgical unit 10 provides the power supply voltage. In another example, an external source provides the power supply voltage to line 162, such as a battery that may be located on the device 70. Further in the example shown, receptacle 174 is electrically coupleable to a reference voltage, such as a signal ground. Receptacle 170 is electrically coupleable to a pull-down resistor $R_0$. The configuration of receptacles 170, 172, 174 is based on techniques used to detect and measure touches on the multivariate controller 100, and thus are for example only and used for the exemplary techniques described here.

In some examples, the generation of RF energy in electrosurgical unit 10 for device 70 creates noise that interferes with the detection and measurement of signals from the multivariate controller 100. In such examples, a low pass filter 190 may be disposed between the drive lines 160, 164 and measurement circuit 180 to filter out noise above a selected cut-off frequency. The low pass filter 190 can be configured as an active low pass filer using operational amplifiers and the operational amplifier circuit, where the capacitance and impedance values of the circuit elements of the low pass filter 190 with the operational amplifier determine the selected cut-off frequency in hertz. Other examples of low pass filters are contemplated. In some example, the measurement circuit 180 and low pass filter 190 can be configured as an adapter circuit having a signal that is output to an electrosurgical unit that does not include features that can accept the electrosurgical unit 70.

The position of the touch within the active portion 122 of transmission element 120 is measured with an analog to digital converter electrically coupled to receptacle 170. Receptacle 172 is set to the high voltage and receptacle 174 is set to a low voltage, such as signal ground. An eight bit analog to digital converter coupled to receptacle 170 can yield a count between 0 and 255, and the value is generally proportional to the distance of touch on the active area 122 from line 160. (Other analog-to-digital resolutions are possible, such as twelve bit and other resolutions.) Therefore, touching one end of the active portion 122 will generate a count at or near 0 and touching the other end of the active portion 122 will generate a count at or near 255. Further, touching an area between the ends of the active portion will generate a count at or near 128. Measurement circuit 180 can be configured to detect the count and provide a corresponding RF signal to electrode 96.

The pressure of the touch on active portion 122 of transmission element 120 is measured with analog to digital converters electrically coupled to receptacles 170, 174. Receptacle 172 is again set to high voltage, but receptacle 174 is coupled to the analog to digital converters instead of ground. A signal, such as voltage, measured at receptacle 174 can be determined as $V_1$, and a signal such as a voltage measured at receptacle 170 can be determined as $V_2$.

In one example no current flows through $R_2$, so the voltage drop across $R_2$ is simply $(V_1-V_2)$. Thus, $$Rp = R0 \frac{V1-V2}{V2}$$

and because force F is generally inversely proportional to Rp (higher resistances result from light touch on the active portion 122), force F can be determined as:

$$F = k\left(\frac{V2}{V1-V2}\right),$$

where k is a constant.

In one particular example, the signals from the transmission element are provided to a low pass filter including an amplifier available under the trade designation AD823AR from Analog Devices, Inc., of Norwood, Mass. An output from the low pass filter, such as low pass filter 190 can be provided to an analog to digital converter in measurement circuit 180, such as a twelve-bit analog to digital converter available under the trade designation AD7992BRMZ-0 also from Analog Devices, Inc. An output from the analog digital converter to a measurement circuit included in measurement circuit 180 can be configured to include a system-on-a-chip microcontroller available under the trade designation 32 Bit AVR Microcontroller AT32UC3C from Atmel Corp. of San Jose, Calif.

Although the present disclosure has been described with reference to preferred embodiments, workers skilled in the art will recognize that changes can be made in form and detail without departing from the spirit and scope of the present disclosure.

What is claimed is:

1. An electrosurgical device operably couplable to an electrosurgical unit, the electrosurgical device comprising:
a handpiece;
an electrode tip extending from the handpiece, the electrode tip configured to deliver an RF signal;
a multivariate controller having a surface in combination with a conductive underside membrane and configured to be responsive to a combination of a variable amount of force on the surface selected from a range of more than two forces and a variable position of the amount of force on the surface selected from a range of positions along the surface such that the multivariate controller is configured to detect the variable position of the amount of force via selective coupling the conductive underside membrane against a conductive substrate operably coupled to a sense line, a first drive line and second drive line, the multivariate controller disposed on the handpiece configured to activate the electrode tip and adjust a setting of the RF signal within a range of settings; and
a plurality of resistor operably coupled to the multivariate controller including a first resistor disposed in parallel between a first drive line and the variable position along the surface and a second resistor disposed in parallel between the second drive line and the variable position along the surface.

2. The electrosurgical device of claim 1 wherein the multivariate controller adjusts a power setting of the RF signal.

3. The electrosurgical device of claim 1 wherein the multivariate controller adjusts a waveform setting of the RF signal.

4. The electrosurgical device of claim 1 wherein the multivariate controller adjusts a fluid flow rate.

5. The electrosurgical device of claim 1 wherein the multivariate controller includes a touch sensor.

6. The electrosurgical device of claim 5 wherein the touch sensor responds to the force.

7. The electrosurgical device of claim 6 wherein the touch sensor responds to a position of the force along an axis of the touch sensor.

8. The electrosurgical device of claim 6 wherein the touch sensor is coupled to a plurality of conductors wherein the touch sensor is activated with a voltage via a first conductor of a plurality of conductors and the force is detected via a second conductor operably coupled to the first conductor.

9. The electrosurgical device of claim 6 wherein the touch sensor includes a potentiometer to detect the force.

10. An electrosurgical device, comprising:
a handpiece,
an electrode tip extending from the handpiece, the electrode tip configured to deliver an RF signal;
a multivariate controller, comprising,
a mounting piece disposed within the handpiece; and
a transmission element disposed on the mounting piece, the transmission element including a surface having a conductive underside membrane facing a conductive substrate operably coupled to a sense line, a first drive line, and a second drive line, the transmission element configured to detect a combination of an amount of force applied to the surface from a range of more than two forces and a variable position of the amount of force on the surface selected from a range of positions and responsively adjust a setting of the RF signal within a range of settings such that the multivariate controller is configured to detect the variable position of the amount of force via selective coupling the conductive underside membrane together with the conductive substrate, the multivariate controller configured to provide a signal representative of the variable position of the amount of force via the first drive line and the sense line; and
a plurality of resistors operably coupled to the multivariate controller including a first resistor disposed in parallel between a first drive line and the variable position along the surface and a second resistor disposed in parallel between the second drive line and the variable position along the surface.

11. The electrosurgical device of claim 10 including a deflectable cover, wherein the transmission element is disposed between the mounting piece and the cover.

12. The electrosurgical device of claim 11 wherein the deflectable cover is planar.

13. The electrosurgical device of claim 11 wherein the deflectable cover is integrally formed with the handpiece.

14. The electrosurgical device of claim 10 wherein the transmission element is urged against the mounting piece.

15. The electrosurgical device of claim 10 wherein the multivariate controller is affixed to the mounting piece with an adhesive.

16. The electrosurgical device of claim 10 wherein the multivariate controller includes a force sensing linear potentiometer.

17. An electrosurgical device, comprising:
a handpiece;
an electrode tip extending from the handpiece, the electrode tip configured to deliver an RF signal;
a multivariate controller having an active surface in combination with a conductive membrane, the multivariate controller including a force sensing linear potentiometer having the conductive membrane disposed proximate a conductive substrate including interdigitated traces coupled to a plurality of drive lines and a sense line, the active surface disposed on the handpiece configured to activate the electrode tip and adjust a setting of the RF signal within a range of settings in response to a combination of a selected amount of a force applied to the active surface from a range of more than two forces and a selected position from a range of positions along the active surface to adjust an impedance such that the multivariate controller is configured to detect the variable position of the amount of force via selective coupling of the conductive membrane together with the conductive substrate, the multivariate controller operably couplable to an electrosurgical unit to provide a signal representative of the variable position of the amount of force via a first drive line of the plurality of drive lines and the sense line and via a second drive line of the plurality of drive lines and the sense line to the electrosurgical unit; and
a plurality of resistors operably coupled to the multivariate controller including a first resistor disposed in parallel between a first drive line of the plurality of drive lines and the variable position along the active surface and a second resistor disposed in parallel between the second drive line of the plurality of drive lines and the variable position along the active surface.

18. The electrosurgical device of claim 17 wherein the force sensing linear potentiometer adjusts the impedance in response to a selected position of the force on the active surface.

19. The electrosurgical device of claim 18 wherein the force sensing linear potentiometer adjusts the impedance in response to the force applied on the active surface along a longitudinal axis of the handpiece.

20. The electrosurgical device of claim 19 wherein the force sensing linear potentiometer adjusts the impedance in response to the force applied along multiple dimensions of the active surface.

21. An electrosurgical device, comprising:
a handpiece;
an electrode tip extending from the handpiece, the electrode tip configured to deliver an RF signal;
a multivariate controller coupled to the handpiece and configured to activate the electrode tip and adjust a setting of the RF signal within a range of settings, the multivariate controller having a conductive substrate in combination with a conductive membrane, the conductive substrate operably coupled to a first conductive drive line, a second conductive drive line, and a sense line wherein the multivariate controller is configured to be responsive to a combination of an amount of force at the touch spot selected from a range of more than two forces and a location of the touch spot selected from a range of locations of the touch spots such that the multivariate controller is configured to detect the amount of force at the variable location touch spot via selective coupling the conductive membrane and the conductive substrate together to provide a signal via the second conductive drive line and the sense line, and
a plurality of resistors operably coupled to the multivariate controller including a first resistor disposed in parallel between the first conductive drive line and the spot and a second resistor disposed in parallel between the second conductive drive line and the touch spot.

22. The electrosurgical device of claim 21 wherein the first drive line is coupled to an activation voltage.

23. The electrosurgical unit of claim 22 wherein the multivariate controller includes a potentiometer, and wherein impedance of the potentiometer is related to force applied to the touch spot.

24. The electrosurgical unit of claim 22 wherein the second drive line and the sense line provide signals indicative of an amount of force applied and a location of the touch spot.

* * * * *